United States Patent [19]
Goldenberg et al.

[11] 4,016,268
[45] Apr. 5, 1977

[54] METHOD OF COMBATTING GASTRIC ULCERATION

[75] Inventors: Marvin M. Goldenberg, Norwich; Leroy J. Honkomp, Oxford, both of N.Y.

[73] Assignee: Morton-Norwich Products, Inc., Norwich, N.Y.

[22] Filed: Oct. 6, 1975

[21] Appl. No.: 619,691

[52] U.S. Cl. .............................. 424/231; 424/232; 424/234; 424/296
[51] Int. Cl.$^2$ ................ A61K 31/29; A61K 31/60; A61K 31/61; A61K 31/625
[58] Field of Search .......... 424/230, 296, 231, 232, 424/234

[56] References Cited
OTHER PUBLICATIONS
Merck Index, 7th Ed. (1960), p. 158.

*Primary Examiner*—Stanley J. Friedman
*Attorney, Agent, or Firm*—Anthony J. Franze

[57] ABSTRACT

Bismuth subsalicylate co-administered with anti-inflammatory drugs combats gastric ulceration associated with such drugs.

1 Claim, No Drawings

METHOD OF COMBATTING GASTRIC ULCERATION

This invention is concerned with a method for combatting gastric ulceration. In particular it is concerned with the use of bismuth subsalicylate to combate the ulcerogenic propensity of widely-used anti-inflammatory drugs.

Commonly used drugs such as aspirin, phenylbutazone, indomethacin, or ibuprofen, while exetrmely valuable for their anti-inflammatory and analgesic effects, are ill suited for long term use because of their tendency to cause gastric ulceration in th host receiving them.

It has now been discovered that bismuth subsalicylate when co-administered perorally with anti-inflammatory drugs such as those aforementioned combats gastric ulceration. Thus, gastric hemorrhagic lesion formation was induced in male Wistar rats by dosing 24-hour fasted animals with a 100 % ulcerogenic does ($UD_{100}$) of an anti-inflammatory drug concomitantly with various dose levels of bismuth subsalicylate. Four hours later, the stomachs were removed and mucosae examined for hemorrhagic lesions and an $ED_{50}$ value obtained by finding that dose of bismuth subsalicylate which inhibited the mean number of lesions by 50%.

The results are set forth in the following table:

Table I

Peroral Protective $ED_{50}$ Values of Bismuth Subsalicylate in Reducing Mean Number of Gastric Hemorrhagic Lesions in Response to Anti-Inflammatory Drugs

| Drug Combination[a] | Dose (mg/kg) | No. of Rats | Mean No. of Lesions per Stomach | Bismuth Subsalicylate $ED_{50}$ Value[b] mg/kg |
|---|---|---|---|---|
| Aspirin[c] + H$_2$O (control) | — | 28 | 4.6 | |
| Aspirin + Bismuth Subsalicylate | 17.5 | 7 | 4.1 | |
| Aspirin + Bismuth Subsalicylate | 43.8 | 7 | 2.3 | 58.6 |
| Aspirin + Bismuth Subsalicylate | 87.5 | 7 | 2.1 | |
| Aspirin + Bismuth Subsalicylate | 109.4 | 7 | 2.0 | |
| Aspirin + Bismuth Subsalicylate | 153.0 | 7 | 0.5 | |
| Phenylbutazone[d] + H$_2$O (control) | — | 26 | 8.1 | |
| Phenylbutazone + Bismuth Subsalicylate | 4.4 | 6 | 6.1 | |
| Phenylbutazone + Bismuth Subsalicylate | 17.5 | 6 | 5.5 | 23.6 |
| Phenylbutazone + Bismuth Subsalicylate | 21.9 | 7 | 4.9 | |
| Phenylbutazone + Bismuth Subsalicylate | 26.3 | 6 | 3.2 | |
| Phenylbutazone + Bismuth Subsalicylate | 43.8 | 6 | 1.8 | |
| Indomethacin[e] + H$_2$O (control) | — | 7 | 3.6 | |
| Indomethacin + Bismuth Subsalicylate | 43.8 | 8 | 1.9 | 39.4 |
| Indomethacin + Bismuth Subsalicylate | 37.5 | 7 | 0.9 | |
| Indomethacin + Bismuth Subsalicylate | 262.5 | 7 | 0.9 | |
| Ibuprofen[f] + H$_2$O (control) | — | 7 | 8.9 | |
| Ibuprofen + Bismuth Subsalicylate | 4.4 | 7 | 6.1 | 11.0 |
| Ibuprofen + Bismuth Subsalicylate | 17.5 | 7 | 3.1 | |
| Ibuprofen + Bismuth Subsalicylate | 43.8 | 7 | 2.7 | |

[a]Bismuth subsalicylate or distilled water administered in combination with each listed anti-inflammatory drug.
[b]Obtained by the Litchfield-Wilcoxon Method using the percentage inhibition of mean number of lesions from control and then finding the dose giving 50% inhibition.
[c]UD100 = 200 mg/kg - 28 of 28 rats with gastric hemorrhagic lesions.
[d]UD100 = 150 mg/kg - 26 of 26 rats with gastric hemorrhagic lesions.
[e]UD100 = 10 mg/kg - 7 of 7 rats with gastric hemorrhagic lesions.
[f]UD100 = 100 mg/kg - 7 of 7 rats with gastric hemorrhagic lesions.

The use of bismuth subsalicylate concomitantly with anti-inflammatory drugs has no adverse effect thereon. That the anti-inflammatory property of aspirin, phenyblutazone, indomethacin or ibuprofen was not impaired by the co-administration of bismuth subsalicylate was demonstrated using the standard carrageenin rat paw edema assay [Winter et. al. Proc. Soc. Exp. Bio. Med. 111:544 (1962)]. Thus, concomitant administration of the protective $ED_{50}$ of bismuth subsalicylate with the anti-inflammatory $ED_{50}$ of aspirin, phenylbutazone, indomethacin or ibuprofen was carried out in the 24-hour fasted male Wistar rat. The percent inhibition of edema formation at 4 and 6 hours after carrageenin administration was determined.

The results are shown in the following table:

Table 2

Anti-Inflammatory Activity in the Carrageenin-Induced Paw Edema Assay in Rats

| Treatment[a] | $ED_{50}$ Values mg/kg | No. of Rats | % Inhibition of Edema Formation[b] 4 hr | 6 hr |
|---|---|---|---|---|
| Aspirin | 167[c] | | | |
| + | + | 8 | 40 | 23 |
| Distilled H$_2$O (control) | — | | | |
| Aspirin | 167 | | | |
| + | + | 8 | 65 | 48 |
| Bismuth Subsalicylate | 58.6 | | | |
| Phenylbutazone | 204[c] | | | |
| + | + | 8 | 52 | 41 |
| Distilled H$_2$O | — | | | |
| Phenylbutazone | 204 | | | |
| + | + | 8 | 65 | 48 |
| Bismuth Subsalicylate | 23.6 | | | |
| Indomethacin | 10[c] | | | |
| + | + | 10 | 58 | 45.5 |
| Distilled H$_2$O | — | | | |
| Indomethacin | 10 | | | |
| + | + | 10 | 61.5 | 48.5 |
| Bismuth Subsalicylate | 39.4 | | | |
| Ibuprofen | 52.1 | | | |
| + | + | 16 | 44 | 40 |
| Distilled H$_2$O | — | | | |
| Ibuprofen | 52.1 | | | |
| + | + | 16 | 52 | 53 |
| Bismuth Subsalicylate | 11.0 | | | |
| Distilled H$_2$O | — | | | |
| + | + | 8 | 11 | 14 |
| Bismuth Subsalicylate | 23.6 or 58.6 | 8 | 11 | 20 |

[a]Drug combinations administered 60 minutes before the injection of carrageenin.
[b]Compared to control (nondrug-treated) hindpaw 4 and 6 hours after carrageenin administration.
[c]Anti-inflammatory $ED_{50}$ value.

The anti-inflammatory drugs are commercially available in number of pharmaceutical dosage forms for oral administration as is bismuth subsalicylate.

What is claimed is:

1. The method of combatting gastric ulceration in a host receiving perorally an anti-inflammatory agent of the group of aspirin, phenylbutazone, indomethacin or ibuprofen which consists in similarly co-administering to said host an amount of bismuth subsalicylate sufficient to combat the gastric ulcerogenic propensity of said anti-inflammatory agent.

* * * * *